United States Patent
Klock (12) 
(10) Patent No.: US 6,287,789 B1
(45) Date of Patent: *Sep. 11, 2001

(54) CHONDROITIN SULFATE AS A MARKER OF BONE RESORPTION

(75) Inventor: John C. Klock, Nicasio, CA (US)

(73) Assignee: BioMarin Pharmaceuticals, Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/246,576

(22) Filed: Feb. 8, 1999

Related U.S. Application Data (63) Continuation of application No. 08/713,403, filed on Sep. 13, 1996, now Pat. No. 5,869,273.

(51) Int. Cl.$^7$ ................................................ G01N 33/532
(52) U.S. Cl. .................... 435/7.21; 436/544; 530/387.5; 530/391.3; 536/123.13
(58) Field of Search .............................. 435/18, 810, 975, 435/7.21; 436/94, 172, 544, 540; 536/123, 123.1, 123.13; 204/452, 461; 530/387.5, 391.3

(56) References Cited

U.S. PATENT DOCUMENTS

| | | | |
|---|---|---|---|
| 4,468,465 | * 8/1984 | Sato | 436/63 |
| 5,019,231 | * 5/1991 | Brandley et al. | 204/182.1 |
| 5,185,245 | * 2/1993 | Heimer | 435/7.1 |
| 5,427,954 | * 6/1995 | Sandy et al. | 436/89 |
| 5,470,578 | * 11/1995 | Aoki et al. | 424/450 |
| 5,869,273 | * 2/1999 | Klock | 435/7.92 |
| 5,948,692 | * 9/1999 | Miyauti et al. | 436/501 |

FOREIGN PATENT DOCUMENTS

| | | | |
|---|---|---|---|
| 0581282 | * | 2/1994 | (EP) . |
| WO95/22765 | * | 8/1995 | (WO) . |

OTHER PUBLICATIONS

Klock et al., "The Difffrent Faces of Disease, Face® Diagnosis of Disease", Glycoimmunology, 2:13–25, 1995.*

Roitt, Essential Immunology, 5th Ed., Blackwell Scientific Publications, pp. 15–17, 1984.*

J. Liu et al, Journ. Chromat., 554, 223–235, 1991.*

* cited by examiner

*Primary Examiner*—David Saunders
(74) *Attorney, Agent, or Firm*—Albert P. Halluin; Luisa Bigornia Howrey Simon Arnold & White, LLP

(57) ABSTRACT

The subject invention provides methods and kits for detecting increased bone resorption in patients. These methods and kits use chondroitin sulfate, a glycosaminoglycan, as a marker for bone resorption. Levels of chondroitin sulfate are detected in samples of urine or serum taken from patients. Measurements of chondroitin sulfate levels are made by methods such as fluorophore-assisted carbohydrate electrophoresis (FACE). Knowledge of increased bone resorption rates is useful in diagnosis of bone disorders such as osteoporosis.

1 Claim, 5 Drawing Sheets

CHONDROITIN SULFATE AS A MARKER OF BONE RESORPTION

CROSS-REFERENCE TO RELATED APPLICATIONS

This application is a continuation of U.S. application Ser. No. 08/713,403, filed Sep. 13, 1996 and U.S. Pat. No. 5,869,273.

1. FIELD OF THE INVENTION

The subject invention is in the field of medical diagnostics and carbohydrate chemistry and biochemistry. In particular, the invention describes the use of chondroitin sulfate, a biological component from human body fluids such as blood and urine, as a marker for bone resorption.

2. BACKGROUND OF THE INVENTION

Carbohydrates play a number of important roles in the functioning of living organisms. In addition to their metabolic roles, carbohydrates are structural components of the human body covalently attached to numerous other entities such as proteins and lipids (called glycoconjugates). For example, human bone consists of hydroxyapatite, minerals, collagen protein, and a proteoglycan matrix. The carbohydrate portion of this proteoglycan matrix imparts essential properties to the bone structure and plays a role in bone metabolism.

Bone resorption is an important process in human health. Children have extremely high bone resorption rates due to their overall high rate of bone metabolism associated with growth. Bettica et al. (1992), Clinical Chemistry 38:2313–2518; Hanson et al. (1992), J. Bone Mineral Res. 7:1251–58. However, in adults, high rates of bone resorption are generally associated with metabolic bone disorders, such as primary hyperparathyroidism, osteomalacia, and Paget's disease. Seyedin et al. (1993), J. Bone Mineral Res. 8:635–41; Hanson et al. (1992), supra. Paget's disease, in particular, is characterized by a very high of bone resorption. Bettica et al. (1992), supra; Seyedin et al. (1993), supra. Although these diseases are significant, they affect a relatively small proportion of the population. The most widespread disease that is associated with a high rate of bone resorption in adults is osteoporosis; however, the increase in bone resorption associated with osteoporosis is much lower than that of Paget's disease, and hence is much more difficult to detect using conventional methods.

Osteoporosis is clinically characterized by low bone mass and abnormalities in the microarchitecture of the bone tissue, which lead to a reduction in skeletal strength and an increased susceptibility to fractures. WHO Technical Report #843 (1994). This disease reportedly affects between 15–20 million Americans (Mundy (1995), in *Bone Remodeling and Its Disorders* (Martin Dunitz Ltd., London), Chap. 12, p. 173), but these numbers may be an underestimate due to the lack of early diagnostic techniques. During the initial stages of this disease, clinical symptoms are subtle and not recognized by the patient. By the time clinical symptoms manifest, a significant amount of bone mass has already been lost. It has been estimated that nearly 45% of American women over the age of 50 have significant reductions in skeletal bone mass, putting them at an increased risk of vertebral, hip, or distal forearm fractures. Melton et al. (1992), J. Bone Mineral Res. 7:1005–10. More than 1.5 million Americans suffer from osteoporotic fractures every year, at an estimated cost to the health care industry of nearly $10 billion. Riggs and Melton (1992), New. Eng. J. Med. 327:620–27; Khosla and Riggs (1995), Mayo Clin. Proc. 70:978–82.

Preventive techniques to control the onset of osteoporosis include estrogen replacement therapy (Bonde et al. (1995), J. Clin. Endocrinol. Metab. 80:864–68; Gambacciani et al. (1994), Obstetrics Gynecol. 83:392–96) and calcium and vitamin D supplementation (Consensus development conference: Diagnosis, prophylaxis, and treatment of osteoporosis (1993), Am. J. Med. 94:646–50; Orimo et al. (1994), Calcified Tissue Int'l 54:370–76). Therapeutic interventions include growth hormone (Kassem et al. (1994), J. Bone Mineral Res. 9:1365–70), fluoride (Khosla and Riggs (1995), supra; Consensus development conference (1993), supra), bisphosphonates (Chestnut et al. (1995), Am. J. Med. 99:144–52; Reid et al. (1994), J. Clin. Endocrinol. Metab. 79:1595–99) and calcitonin (Khosla and Riggs (1995), supra).

These prevention and intervention therapies require accurate and sensitive measures of bone formation and bone resorption to be able to adequately assess their immediate and long-term efficacy. One of the best measures of susceptibility to fractures is assessment of bone mass or bone mineral density. WHO Technical Report #843 (1994). Although this method of monitoring bone mineral density yields measurements which have been shown to be highly correlated with bone strength, they do not provide information on the dynamics of bone resorption versus bone formation. Radiological techniques also provide information only about selected skeletal sites, complicated by the fact that each site has a different ratio of trabecular to cortical bone, which in turn have different rates of loss. Mundy (1995), supra. Most importantly, radiological techniques are relatively insensitive to changes in bone density which occur over time periods of less than one year. Measuring changes in bone density at intervals of more than one year, however, can result in significant bone loss before the disease is detected and treatment initiated. This measurement time lag also creates difficulties in assessing the efficacy of treatment interventions. It is clear that more accurate and sensitive methods for early detection of osteopenia and the subsequent risk for development of osteoporosis are needed.

A number of new biochemical markers for bone have been proposed for estimating rates of bone resorption, with the hope of allowing for early prediction of bone loss rather than later observation of reduced bone mineral density. Biochemical tests for bone resorption which are currently being tested include urinary hydroxyproline (Reeve et al. (1995), Calcified Tissue Int'l 57:105–10), serum cross-linked N- and C-telopeptides of type I collagen (Gertz et al. (1994), J. Bone Mineral Res. 9:135–42; Valimaki et al. (1994), Eur. J. Endocrinol 131:258–62), and urinary pyridinium cross-links (Valimaki et al. (1994), supra). These tests have become the most commonly discussed methods for detecting bone resorption and osteoporosis. For example, reviews of the currently known methods for detecting osteoporosis may be found in Valimaki et al. (1994), supra; Reeve et al. (1994), supra; Garnero et al. (1994), J. Clin. Endocrinol. Metab. 79:1693–1700; McCarroll (1993), Analytical Chem. 65:388R–95R (review article); Bettica et al. (1992), supra. However, these tests have high within-subject variability. Furthermore, most urinary biochemical markers are normalized to creatinine to account for daily fluctuations in urine concentration. This normalization creates several problems, such as particularly high variation between samples collected at different times during the day (sometimes as high as 30%). This problem is most serious if excretion rates of abnormals and normals are fairly close, because a high coefficient of variation between samples would tend to produce higher numbers of false negatives.

In view of the problems of these markers, diagnosis would be helped greatly if more sensitive and convenient techniques could be developed for the screening and diagnosis of osteoporosis. In assessing these new tests, it is important to establish that they can, in practice, be used to monitor the development of osteoporosis. Falch (1994), Scand. J. Clin. Lab. Invest. (Suppl. 219) 54:40–41; Farley and Baylink (1995), Clin. Chem. 41:1551–53. The validation of these new urine and serum assays is perhaps even more urgent due to the need for immediate clinical assessment of emerging new treatments of osteoporosis. Garnero et al. (1994), supra. Ideally, these tests should be noninvasive, convenient, accurate, sensitive, specific to the disease process, and economical.

Several authors have speculated that glycosaminoglycans (GAGS) as a broad chemical class could be evaluated as biochemical markers for bone turnover. Larking et al. (1987), Biochem. Med. Metabol. Biol. 37:246–54; Todorova et al. (1992), Horm. Metab. Res. 24:585–87; McCarroll (1993), supra. GAGs are carbohydrates which are integrally related to collagen and comprise a portion of proteoglycans found in connective tissue and bone. Mundy (1995), supra. Specifically, GAGs are sugar chains consisting of repeating polymers of acidic polysaccharides. These materials are composed of building blocks of the following sugars in various combinations: galactose, glucose, N-acetylglucosamine, N-acetylgalactosamine, glucuronic acid, galacturonic acid and iduronic acid. In addition, these sugar units may be variably linked $\alpha$ or $\beta$ at their anomeric carbons and (1–3) or (1–4) to their ring carbons through an O-glycosidic bond. Finally they may be variably substituted with sulfates at their 2,3,4 or 6 carbons. Depending on the precise repeating disaccharide structure and location of sulfates, human connective tissue GAGs are commonly classified as chondroitin sulfates, dermatan sulfates, heparan sulfates, heparin sulfates and keratan sulfates. Collins (1987), *Carbohydrates* (Chapman Hall, London). Degradation products of these GAGs are found in human urine and serum, with chondroitin sulfate being the major GAG of normal urine (Poulsen (1981), Scand. J. Clin. Lab. Invest. 41:675–81).

One method of measuring individual carbohydrates in a sample is by FACE, an acronym standing for the technique of Fluorophore-Assisted Carbohydrate Electrophoresis. The FACE technique is described in detail in U.S. Pat. Nos. 4,975,165, 5,035,786, 5,104,508, 5,109,231, 5,205,917, 5,316,638, 5,340,453, 5,472,582, and 5,087,337. However, until the present invention, no one has been able to use FACE (or for that matter, any other technique) to assay accurately the levels of specific GAGs in urine. Additionally, those skilled in the art believed other biochemical markers were more suitable than GAGS for assaying bone resorption, and so most references teach the use of these other markers. Indeed, in 5 articles comparing biochemical markers of bone resorption (Valimaki et al. (1994), supra; Reeve et al. (1994), supra; Garnero et al. (1994), supra; McCarroll (1993), supra; Bettica et al. (1992), supra), and only one mentions GAGs (McCarroll (1993), supra) and only in passing. Moreover, no one, until the present invention, even discusses chondroitin sulfate specifically as a potential biochemical marker.

3. SUMMARY OF THE INVENTION

Figure 1:
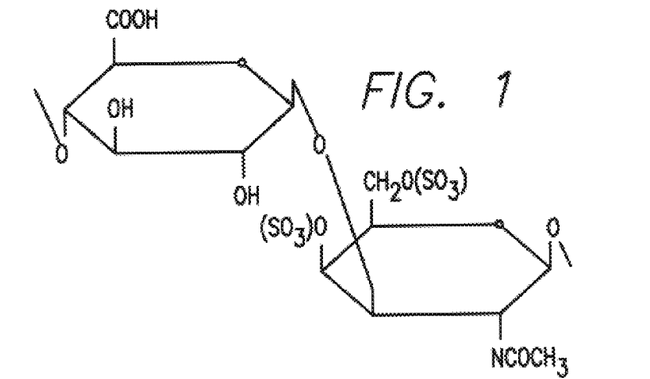
FIG. 1. The structure of a chondroitin sulfate disaccharide.

Reported herein for the first time is chondroitin sulfate as a biochemical marker for bone resorption. Chondroitin sulfate is a common carbohydrate found in all mammalian connective tissues; it is a polymer of disaccharides having the structure [-glucuronic acid $\beta(1-3)$-N-acetylgalactosamine-4-sulfate $\beta(1-4)$-]$_n$; [-glucuronic acid $\beta(1-3)$-N-acetylgalactosamine-6-sulfate $\beta(1-4)$-]$_n$; and [-glucuronic acid $\beta(1-3)$-N-acetylgalactosamine-4,6-sulfate $\beta(1-4)$-]$_n$, as shown schematically in FIG. 1. The present invention is based, in part, on the discovery that chondroitin sulfate is a remarkably reliable marker for detecting bone resorption. Additionally, the present invention demonstrates that, as a marker, chondroitin sulfate has reduced within-subject variability and its level varies in concert with creatinine. Hence, it can be normalized to creatinine without the high variation seen with other biochemical markers.

The invention is based, in part, on the development of methods for accurately measuring chondroitin sulfate levels in patient samples, including but not limited to blood, urine, and saliva, and the recognition that levels of this marker are highly correlated to the process of bone resorption. Evaluation of levels of chondroitin sulfate in patient samples can therefore be used as an innovative new screening and diagnostic tool for detecting changes in bone turnover which occur during the manifestation of many bone disorders, especially osteoporosis. Importantly, these markers will not only enhance the ability of clinicians to monitor patient compliance to therapeutic interventions, but they will also provide convenient and sensitive early indicators of the therapeutic response of individual patients.

One aspect of the present invention provides easy methods for identifying and quantitating chondroitin sulfate as a novel marker for bone resorption. One particularly useful method for assaying the chondroitin sulfate marker is by using a fluorophore labeling technique called FACE, which stands for Fluorophore-Assisted Carbohydrate Electrophoresis. In alternative aspects of the invention, the chondroitin sulfate can be assayed using a wide variety of different labels, including but not limited to a chromophore label, a radioactive label, or a chemiluminescent label; the chondroitin sulfate is then detected by an appropriate detection technology. The labeled chondroitin sulfate marker is itself another aspect of the present invention.

Another aspect of the invention is the use of kits to carry out analysis of chondroitin sulfate levels in a body fluid.

4. BRIEF DESCRIPTION OF THE FIGURES

FIG. 2. Measurement of chondroitin sulfate added to urine samples.

5. DETAILED DESCRIPTION OF THE INVENTION

The subject invention provides a method for using chondroitin sulfate as a marker for measuring bone resorption in an individual. To this end, the subject invention provides for the testing or analysis of chondroitin sulfate to determine the presence and quantity of this substance in body fluids. A principal feature of the subject invention is the specific detection and identification of chondroitin sulfate. As an aspect of the method, the subject invention further includes compositions of chondroitin sulfate labeled for use as a marker and kits for performing the method.

5.1. Definitions

The testing or analysis of chondroitin sulfate provides for the convenient diagnosis of a number of human and animal bone disorders. By diagnosis of a disorder, it is intended not simply the identification of a disorder that has manifested symptoms, but also the identification of a variety of adverse physiological conditions, including the physiological conditions of individuals that have a propensity to develop a disorder, i.e., prognostic uses, the identification of individuals possessing the genetic capacity to transmit a disorder to descendants, and the identification of individual exposures to toxic chemicals. Furthermore, for the purpose of this application, the term "disorder," when used nonspecifically, includes those physiological conditions that are capable of being identified by diagnosis. Individuals manifesting a disorder for diagnosis are defined to be "afflicted" individuals. The terms "individual" and "patient" include animals, especially mammals, and particularly humans.

5.2. Chondroitin Sulfate

A principal feature of the subject invention is the measurement of the levels of the diagnostic carbohydrate chondroitin sulfate present in a sample isolated from an individual suspected of being afflicted. The term "chondroitin sulfate," unless further specified, includes carbohydrates alone (in the form of poly-, oligo-, or disaccharides) and glycoconjugates that include chondroitin sulfate such as glycoproteins, glycolipids, proteoglycans, and the like.

The chondroitin sulfate may be covalently joined to polypeptides or lipids, or may be independent of other molecules. The chondroitin sulfate in a sample from an afflicted individual may be present in a concentration that is either higher or lower than the chondroitin sulfate present in a sample from in an unafflicted individual. The difference in chondroitin sulfate concentration between afflicted and unafflicted individuals does not necessarily exist in all body tissues.

5.3. Analysis of Disorders

The subject invention measures chondroitin sulfate levels in order to detect bone resorption. In one embodiment of the invention, the detection of bone resorption is used to assess the status of a bone disorder, such as Paget's disease, primary hyperparathyroidism, osteomalacia, or, especially, osteoporosis.

Chondroitin sulfate is especially useful as a marker for bone disorders because it demonstrates extremely low within-subject and analytical variability, unlike other currently available biochemical markers. In addition, the biochemical nature of the assay system allows for the quantitation of chondroitin sulfate in serum samples, which could further reduce the variation found in urine markers. Furthermore, urinary and serum GAGs are stable and not affected by long-term frozen storage or by repeated freezing and thawing. Thus, chondroitin sulfate is an excellent biochemical marker for bone resorption. Determination of chondroitin sulfate will have substantial clinical and research utility due to its increased sensitivity and low variability and could be used not only to monitor the osteoporotic disease process itself, but also to assess risk factors, lifestyle behaviors, and the effects of hormone replacement therapy on the process of bone turnover.

The subject invention can be used to measure bone resorption, and assess the status of bone disorders, in many different types of animals. Preferred animals are vertebrates, especially mammals, and particularly humans.

5.4. Normalization of Chondroitin Sulfate to Creatinine

In animals (including humans), the concentration of urine varies throughout the course of a day. To correct for this concentration variance, measurements of substances from urine samples are frequently normalized to creatinine levels in the samples, as creatinine production in muscle is relatively constant during the day. In a preferred embodiment of the subject invention, the amount of chondroitin sulfate measured in a sample is expressed relative to the amount of creatinine in the sample. This is particularly advantageous in the context of chondroitin sulfate, since chondroitin sulfate excretion rates closely parallel creatinine excretion. This tight linkage results in an extremely low within-subject coefficient of variation of the chondroitin sulfate/creatinine ratio (10%) as measured in urine samples collected either once daily for a week or multiple times within a 24-hour period. Adjusting most urinary biochemical markers for creatinine creates several problems, in particular high variation between samples collected at different times during the day (some as high as 30%), which tends to produce higher numbers of false negatives. However, the test for chondroitin sulfate that is provided by the present invention greatly reduces this problem and allows for the accurate detection of those with abnormally high bone resorption.

5.5. Analysis of Chondroitin Sulfate levels

Chondroitin sulfate may be assayed using a variety of ways. For example, the chondroitin sulfate level in a sample may be assayed by separating, detecting, and quantitating the chondroitin sulfate present. Labeling of the chondroitin sulfate may be performed before or after separation from other constituents in a sample. Alternatively, the amount of chondroitin sulfate in a sample may be assessed without necessarily separating the chondroitin sulfate from the other sample constituents, for example, by an ELISA (enzyme-linked immunoassay) procedure.

In one embodiment of the subject invention specifically exemplified below, the concentration of chondroitin sulfate in a sample is measured by fluorophore-assisted carbohydrate electrophoresis ("FACE"). The fluorophore-assisted carbohydrate electrophoresis technique is described in detail in U.S. Pat. Nos. 4,874,492, 5,104,508, and 5,205,917, which are herein incorporated by reference. Fluorophore-assisted carbohydrate electrophoresis permits the electrophoretic separation of a complex mixture of carbohydrates into distinct bands on a gel or similar electrophoretic matrix such as capillary electrophoresis.

5.5.1. Sample Preparation

Samples for analysis of chondroitin sulfate may be prepared from many tissues or bodily fluids removed from individuals. Tissues or bodily fluids for analysis necessarily contain at least chondroitin sulfate. Suitable tissues or body fluids for analysis include blood, saliva, tears, urine, skin, muscle, bone marrow, cerebrospinal fluid, synovial fluid, lymphatic fluid, amniotic fluid and the like. Preferred tissues or bodily fluids for analysis are those tissues conveniently obtained from patients, especially urine, blood and saliva. Factors affecting the choice of tissues for analysis include: the quantity of diagnostic carbohydrates present in the sample, the quantity of background carbohydrates in the sample, and the presence of molecules in the sample capable of interfering with separation of the diagnostic carbohydrates.

Samples for analysis may be used directly, or may require processing prior to the separation and quantitation of the chondroitin sulfate. The precise method of sample processing employed for a given sample may vary in accordance with a number of factors attributable to the choice of the source material, the nature of the material being assayed, and the type of substitutions suspected. These factors include: any required release of chondroitin sulfate from biologic sources, the concentration of the chondroitin sulfate, the concentration of background carbohydrates, the presence of interfering molecules (i.e., molecules that adversely affect chondroitin sulfate band mobility or the labeling of the chondroitin sulfate), whether the chondroitin sulfate is bound to cells, whether the chondroitin sulfate is free or bound to other molecules, and the like. Suitable methods for processing samples include: dialysis, to remove interfering molecules; ultrafiltration, to concentrate carbohydrates and remove interfering molecules; centrifugation, to remove interfering particulates or concentrate cells; precipitation, to remove interfering molecules; and detergent solubilization, to release carbohydrates from cells. In one embodiment of the subject invention, glycosaminoglycans (including chondroitin sulfate) are precipitated from the sample prior to further analysis; for example, the precipitation may be carried out using cetylpyridinium chloride (CPC) reagent.

It may be advantageous to modify the structure of some carbohydrates by means of cleavage between carbohydrate subunits prior to separation. Suitable methods of cleavage include the use of acids, bases, and glycosylytic enzymes, either endoglycosidases or exoglycosidases. Reasons for treatment of samples include the liberation of linked disaccharides from glycoconjugates and the generation of chondroitin sulfates that have a more convenient migration rate, i.e., better separation from other carbohydrates. Similarly, it may be advantageous to use glycosyltransferases along with donor sugar, if required to produce a more convenient migration rate. In one embodiment of the invention described herein by way of example, the sample is treated to convert the full-length chondroitin sulfate into chondroitin sulfate disaccharides, especially by digesting the sample with a chondroitinase, particularly chondroitinase ABC or a biological extract containing chondroitinase ABC.

5.5.2. Sample Labeling

In a preferred embodiment of the subject invention, the prepared samples are labeled to facilitate identification. Labeling may be accomplished covalently or non-covalently. For example, samples may be non-covalently labeled by means of a biological probe which specifically recognizes a region of chondroitin sulfate such as an antibody or the binding domain of an enzyme, i.e. chondroitinase or a sulfotransferase. Labeling may be performed before or after purification, or partial purification, of chondroitin sulfate from the sample.

5.5.2.1. Fluorophore Labeling

Prior to electrophoresis, a prepared sample of a carbohydrate mixture for analysis is treated with a fluorophore label that combines with the reducing end of the carbohydrates for analysis. The fluorophore label permits the quantitative measurement of the labeled carbohydrates by fluorescence. The fluorophore label either is charged or coupled with a charge-imparting species when the fluorophore itself is uncharged. Thus the label not only fluorescently tags the carbohydrates, it also imparts an ionic charge, permitting hitherto uncharged carbohydrates to migrate in an electric field. A description of fluorophores suitable for use in the subject invention can be found in U.S. Pat. Nos. 5,035,786, 5,472,582 and 5,340,453, and PCT application WO 91/05256, which are herein incorporated by reference. Preferred fluorescent labels include 8-aminonaphthalene-1,3,6-trisulphonic acid (ANTS), 1-amino-4-naphthalene sulfonic acid (ANSA), 1-amino-6,8-disulphonic acid (ANDA), lucifer yellow, and 2-aminoacridone (AMAC). In one embodiment, the label is covalently attached to the chondroitin sulfate; in an alternative embodiment, the label is attached via a biological probe or periodate. The subject invention further includes chondroitin sulfate labeled with any of the above fluorescent labels, attached covalently or via antibody or periodate, for use as a marker in measuring bone resorption.

5.5.2.2. Non-Fluorophore Labeling

Alternatively, chondroitin sulfate may also be labeled using a non-fluorophore label. The label is preferably a label capable of reacting with the reducing end of chondroitin sulfate carbohydrate, such as a primary amine, and further capable of being detected by a detection technology. Alternatively, the label may be attached to the chondroitin sulfate via a biological probe or via periodate. The label may be a chromophore label, a chemiluminescent label, a radioactive label, or a charged material.

For example, appropriate chromophores include those which have a primary aryl amine so as to be effective labeling agents. These can be found as a large group in section 8 of the Molecular Probes Co. Catalog (Copyright 1992, Eugene, Oregon, pages 47–49). Such materials include aminocoumarin derivatives, aminoeosin, aminodeoxydigoxigenin, amiononaphthalamide, aminoanilines, biotin ethylenediamine, aminocadaverine, avidin and biotin amino derivatives, cascade blue, lucifer yellow, aminorhodamines, hydrazines and many others. These materials are bound to the chondroitin oligosaccharide at the reducing end of the sugar using reductive amination chemistry which is a commonly used methodology. Additionally treatment of the vicinal hydroxyls of the chondroitin sugar units with periodate can create sites for reductive amination. In some cases there may be the need to separate the unbound label from the labeled material prior to detection using a UV-visible spectrophotometric device. Each of these aminated chromophoric labels has at least one absorption maximum for detection of labeled chondroitin sulfate. Further, the labels herein described as ANTS and AMAC also can be detected using UV or visible absorption devices, since these compounds adsorb in this spectral range an addition to being fluorophores.

The subject invention further includes chondroitin sulfate labeled with any of the above labels, attached covalently or via antibody or periodate, for use as a marker in measuring bone resorption.

5.5.3. Sample Separation

In embodiments of the subject invention, the labeled chondroitin sulfate is separated by electrophoresis.

Alternatively, chondroitin sulfate may be separated, either labeled or prior to labeling, by related technologies or by chromatography.

5.5.3.1. Electronic Separation

In one embodiment of the methods of the invention, the labeled sample is subjected to electrophoretic separation, in order to separate and concentrate the labeled carbohydrates into bands. The carbohydrate electrophoresis may be accomplished using gel electrophoresis, such as polyacrylamide gel electrophoresis; in an alternative embodiment, the electrophoresis is accomplished using electrophoretic techniques and media which are different from conventional gel electrophoresis. Advantages of using other media include ability to analyze smaller sample sizes and the ability to use reverse flow osmotic techniques, colloidal or micellar solutions, or alternative stationary or mobile phase affinity resins to enhance separations and to promote the ability to semiautomate the examination of carbohydrates. A preferred alternative embodiment for performing fluorophore-assisted carbohydrate electrophoresis is capillary electrophoresis ("CE"). The term CE includes capillary zone electrophoresis, isoelectric focusing, capillary gel electrophoresis, isotachophoresis, and micellar CE. CE is particularly suitable for semiautomated or fully automated analytical procedures, and CE methodology is beginning to replace HPLC in many clinical labs. The separation of carbohydrates using CE has been described in recent publications, such as Honda et al. (1990), Anal. Biochem. 191:228–34; and Liu et al. (1991), J. Chromatography, 559:223–35.

When performing the chondroitin sulfate analysis, the electrophoretic separation should take place to an extent sufficient to independently resolve bands of diagnostic carbohydrates specific for the disorder of interest. Electrophoresis may proceed past the point where some carbohydrates have been removed from the electrophoresis separation medium. Electrophoresis may be performed in one or in more than one dimensions, preferably in one or two dimensions. Two-dimensional separation of carbohydrates by fluorophore-assisted carbohydrate electrophoresis is described in U.S. Pat. No. 4,975,165, which is herein incorporated by reference.

After the chondroitin sulfate has been separated from other carbohydrates by electrophoresis, the chondroitin sulfate may be subsequently transferred in situ on to a immobilizing matrix such as a nitrocellulose or nylon membrane by electroblotting or the like. Membranes containing the immobilized chondroitin sulfate (as well as other carbohydrates in the original mixture) may subsequently by probed with antibodies or similar specific binding reagents so as to indicate the presence and quantity of chondroitin sulfate. The transfer of electrophoresis-separated carbohydrates onto immobilizing matrices is described in detail in U.S. Pat. No. 5,019,231, which is herein incorporated by reference.

5.5.3.2. Chromatographic Separation

In an alternative embodiment of the subject invention, the sample containing chondroitin sulfate is separated by chromatographic methods. These methods include any type of chromatography that is capable of separating the chondroitin sulfate, either labeled or prior to labeling, from other constituents present in the sample. For example, these methods may include size-exclusion chromatography, ion-exchange chromatography, and other types of chromatography, as well as combinations of these chromatographic methods. Further, in a modification of a chromatographic technique, one may separate chondroitin sulfate by adsorbing sample onto a charged substrate, for example, a "dip-stick," or the well of a microtiter plate. Buffer conditions, such as ionic strength and pH, may be easily optimized by one of ordinary skill in the art for the separation of chondroitin sulfate given the teachings presented herein. For example, one may use the FACE technology described herein for detection of chondroitin sulfate as an assay in order to optimize conditions for chromatographic purification and detection of chondroitin sulfate. One skilled in the art will also quickly recognize many obvious variations on these separation methods, and all such variations are intended to be covered by the scope of the subject invention.

5.5.4. Detection and Quantitation

The exact method of detecting and quantitating chondroitin sulfate in a sample will depend upon the particular technique chosen to assay this carbohydrate. For example, following separation of fluorescently labeled carbohydrates on a gel, the carbohydrates may be visualized directly by fluorescence under U.V. light and the banding patterns stored photographically. Alternatively the separated carbohydrates may be visualized by photoelectric means, including laser-scanner photomultiplier tube systems and cooled charge coupled devices (CCD). CCDs are semiconductor imaging devices that permit the sensitive detection of emitted light. CCDs and their uses are described in U.S. Pat. Nos. 4,874,492 and 4,852,137 which are herein incorporated by reference. The image produced by the CCD may be subsequently transferred to a computer and analyzed by image analysis software such as Glyko® FACE analysis software, or similar image analysis programs. These systems for the imaging and analysis of gels are commercially available from Glyko, Inc. (Novato, Calif.). The data may be subjected to analysis by a variety of software programs. Software programs of interest include those with the ability to quantitate peak or band intensity, measure band mobility or column retention time, determine the relative molecular weight of carbohydrates forming bands or peaks, compare the standards with the samples for analysis, remove unwanted background information, and perform various forms of statistical analysis.

Alternatively, and for carbohydrates not separated on gels, the quantitation of labeled chondroitin sulfate may be performed by detection with a detector that measures UV absorbance. The detector may be either a fixed wavelength or variable wavelength detector, and it preferably generates data that is stored and analyzed by a computer. The labeled chondroitin sulfate also may be induced to fluoresce by a laser light source or by a noncoherent light source; in either case, the induced fluorescence can be detected on a detector having a variable or fixed wavelength. The detector preferably generates data that is stored and analyzed by a computer.

For chondroitin sulfate labeled by a non-fluorophore label, other detection methods may be applied. For example, radioactive labels may be detected by scintillation counting or autoradiographic means; chromatophore labels may be detected with various light-sensitive instruments; and chemiluminescent labels may, following treatment with the proper luminescence-inducing chemicals, be detected with spectrophotometers and related instruments. One skilled in the art will quickly recognize many obvious variations on these detection methods, and all such variations are intended to be covered by the scope of the subject invention.

Data generate by any of these means may optionally be normalized to creatinine, as described in section 5.4 above.

5.5.5. Standards

In an embodiment of the invention, diagnostic standards are included with the analysis of the chondroitin sulfate in the patient samples; however, the information embodied by the diagnostic standard, e.g., band migration distance and intensity, may also be obtained from comparison with stored records made from diagnostic standards previously subjected to analysis under conditions similar to the conditions to which the patient samples are exposed. Diagnostic standards may be both positive (i.e., corresponding to the complete carbohydrate pattern in an afflicted individual) and negative (i.e., corresponding to unafflicted individual). Diagnostic standards may have a composition similar to that of samples for analysis in that they may contain both chondroitin sulfate and background carbohydrates with composition similar to that found in actual samples. Diagnostic standards may be derived from samples obtained from afflicted and unafflicted individuals. Alternatively, diagnostic standards may contain chondroitin sulfate free of background carbohydrates.

Diagnostic standards may be labeled prior to the labeling of the samples for analysis; however, diagnostic standards are preferably labeled concomitantly with the labeling for the standards for analysis. Furthermore, the chondroitin sulfate in the standards is preferably quantitated so as to provide for quantitative or qualitative comparisons with the amount of chondroitin sulfate in the patient samples.

In an alternative embodiment, the standard may be a specific reference level of chondroitin sulfate, preferably normalized to creatinine. The reference level is preferably calculated from a reference population, or alternatively may be calculated from a reference individual. The reference level is preferably calculated from samples analyzed at the same time as the patient samples, or alternatively is calculated from samples analyzed prior to analysis of the patient samples.

5.6. Diagnostic Kits

The subject invention also includes kits for assaying for the presence of chondroitin sulfate, for the analysis of medical samples or human or animal-derived material for the purposes of medical diagnosis, and for the synthesis or manufacture of carbohydrates. Fluorophore-assisted carbohydrate electrophoresis diagnosis kits provide collections of reagents required for performing fluorophore-assisted carbohydrate electrophoresis diagnosis. Suitable kits enable laboratories to conveniently perform fluorophore-assisted carbohydrate electrophoresis diagnosis, fluorophore-assisted carbohydrate electrophoresis-CE, or some other method, and may include reagents for performing tests to identify one or more specific disorders or disease states. Kits may include diagnostic standards, fluorescent label and associated labeling chemicals, blotting and binding materials (e.g., membranes), carbohydrate-specific binding reagents, instructions, sample containers, capillary columns of different constructions and coatings or fillings, polyacrylamide gel reagents, precast gels, enzyme buffers, reducing agents (for use in the fluorophore labeling of carbohydrates), and enzymes capable of catalyzing reactions that structurally alter the chondroitin sulfate.

In one embodiment, the kit contains a chondroitinase and a label for carbohydrate labeling. Further, the kit may contain a highly charged substrate for binding the chondroitin sulfate in a sample. For example, the charged substrate may be a membrane on a "dip-stick," which is inserted into the sample. The label can be a fluorescent label, a chromophore label, a radioactive label, or a chemiluminescent label. Preferably, the label is a fluorescent label chosen from the group 8-aminonaphthalene-1,3,6-trisulphonic acid (ANTS), 1-amino-4-naphthalene sulfonic acid (ANSA), 1-amino-6,8-disulphonic acid (ANDA), lucifer yellow, and 2-aminoacridone (AMAC). Suitable chondroitinases are chondroitinase ABC or a biological extract containing chondroitinase ABC. In a particular embodiment, the label is 8-aminonaphthalene-1,3,6-trisulphonic acid (ANTS) and the chondroitinase is chondroitinase ABC or a biological extract containing chondroitinase ABC. In an alternative embodiment, the label is attached to an antibody that binds chondroitin sulfate. Preferably, the kit further contains a chondroitin sulfate standard. Kits may optionally include instructions for performing the chondroitin sulfate assay for bone resorption.

More complete kits may include equipment for performing fluorophore-assisted carbohydrate electrophoresis or fluorophore-assisted carbohydrate electrophoresis-CE, such as polyacrylamide gel apparatus, capillary electrophoresis apparatus or components thereof, liquid handling materials, detectors, lasers, CCDs, computers, software, and the like. Reagents included in fluorophore-assisted carbohydrate electrophoresis diagnosis kits or fluorophore-assisted carbohydrate electrophoresis-CE diagnosis kits may be conveniently provided in premeasured amounts. The kits preferably include instructions for carrying out the fluorophore-assisted carbohydrate electrophoresis method or fluorophore-assisted carbohydrate electrophoresis-CE method of the present invention.

The invention having been described, the following examples are offered to illustrate the subject invention by way of illustration, not by way of limitation.

6. EXAMPLES

6.1. Measurement of Chondroitin Sulfate in Human Urine

In order to use chondroitin sulfate as a marker for bone resorption, it was necessary to verify that it could be detected in the context of human urine. For this purpose, varying amounts of chondroitin sulfate were added to normal urine. This added chondroitin sulfate was then detected and quantitated using FACE technology.

6.1.1. Materials and Methods

Urine samples (0.5 ml) were spiked with varying amounts (0.1–10.0 $\mu$g) of chondroitin sulfate (Sigma Chemical Co., St. Louis, Mo.). High molecular weight glycosaminoglycans (GAGs) were precipitated from the urine samples by adding 0.5 ml of cetylpyridinium chloride (CPC) reagent (0.2M NaCitrate, 0.1% CPC, pH 4.8) and incubating for 30 minutes at 37° C. The CPC precipitate was recovered by centrifugation for 5 min at 14,000×g, and the supernatant was discarded. The CPC pellet was washed by dissolving the pellet in 67 $\mu$l 2 M LiCl, adding 267 $\mu$l cold ethanol, and re-precipitating for 2 hr at 4° C. The washed pellet was recovered by centrifugation for 5 min at 14,000×g and resuspended in 50 $\mu$l $H_2O$. Urinary GAGs were then digested by adding 10 milliunits of chondroitinase ABC (Sigma Chemical Company, St. Louis, Mo.) in a 20 $\mu$l volume, and incubating for 30 min at 37° C. The digest was dried in a centrifugal vacuum evaporator and the disaccharides were then fluorescently labeled by resuspending the residue in 5 $\mu$l of the fluorophore 8-aminonaphthalene-1,3, 6-trisulphonic acid (ANTS) (0.15M in 15% acetic acid) and 5 μl of 1 M NaCNBH$_4$ in DMSO. The labeling reaction was complete in 2 hours at 45° C. The vial of labeled oligosaccharides was brought to 20 μl in 10% glycerol and a 4 μl aliquot was removed for analysis.

Unique, fluorescently tagged chondroitin sulfate disaccharide bands were then separated and quantitated using a FACE system apparatus (Glyko, Inc., Novato, Calif.). The 4 μl aliquot was placed in a lane of a FACE pre-cast polyacrylamide gel and electrophoresed for 1.5 hours using 50 mM Tris-tricine, pH 10.4, as a buffer. Detection and quantitation were performed by placing the gel into a FACE SE1000 imaging system (Glyko, Inc., Novato, Calif.), which uses a charge-coupled device to create electronic images of fluorescent bands present on the gel. These electronic images were then processed into a digital image which was displayed on a computer screen using FACE Imaging Software (Glyko, Inc., Novato, Calif.). The software allowed for quantitation of the chondroitin sulfate disaccharide band and recognition of the band pattern compared to a ladder of glucose polymers which were run in a single lane of the gel in parallel with the sample.

6.1.2. Results

Figure 2A:
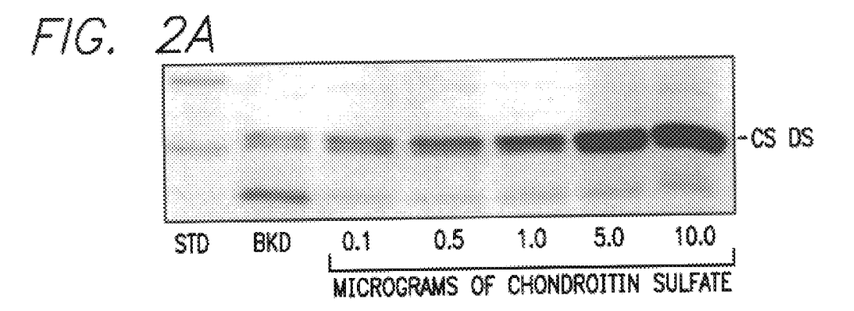
FIG. 2A. FACE gel showing detection of the chondroitin sulfate disaccharide (CS DS).
Figure 2B:
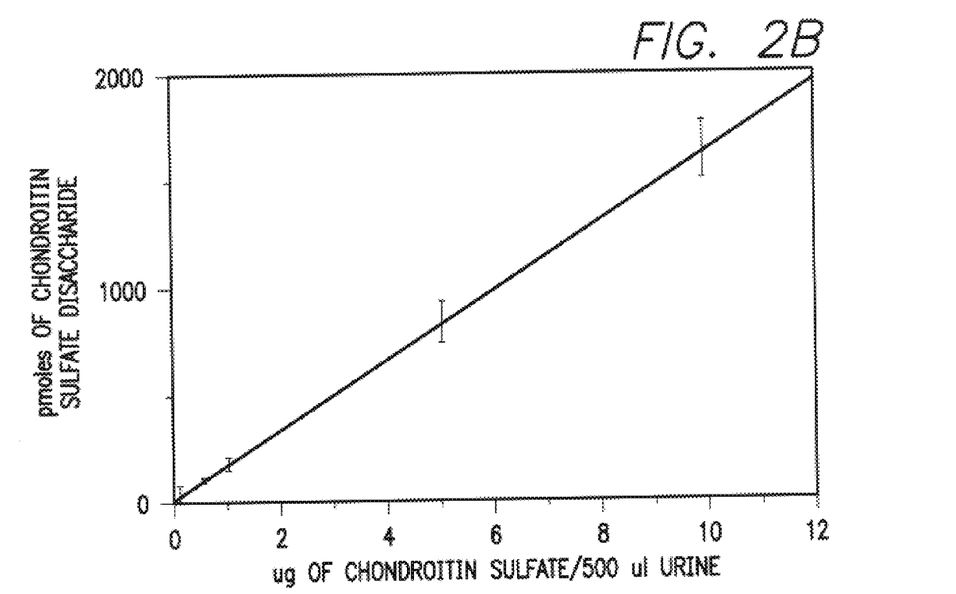
FIG. 2B. Graph of amount of chondroitin sulfate added to urine versus amount of chondroitin sulfate disaccharide detected by FACE, as assayed by densitometric measurement of the gel shown in FIG. 2A.

Results of these dose response validation studies are shown in FIG. 2. FIG. 2(A) shows the band patterns of chondroitin sulfate disaccharide (CS DS) obtained from this dose response test. The amount of chondroitin sulfate disaccharide in each lane was quantitated by digitization and the data was used to generate the dose response plot shown in FIG. 2(B). As can be seen, there was a high correlation between the amount of chondroitin sulfate added to the urine sample and the amount measured by the assay. In addition, this experiment demonstrated that the FACE assay for chondroitin sulfate is linear over at least two orders of magnitude.

6.2. Measurement of Urinary Chondroitin Sulfate in Normal and Osteoporotic Women Having established that added chondroitin sulfate could be reliably detected and quantitated from human urine, actual patient urines were assayed for chondroitin sulfate. Samples from patients who potentially had osteoporosis and from normal individuals were both tested.

6.2.1. Materials and Methods

Urine samples were collected at various time periods from normal individuals and from patients diagnosed with osteoporosis. Urine samples were stored at −70° C. until time of assay, then thawed and filtered prior to use (ULTRA-FREE-MC, 30,000NMWL Filter; Millipore, Bedford, Mass.). GAGs were precipitated, digested, and labeled with ANTS as described in section 6.1.1. Separation, detection and quantitation of the fluorescently tagged oligosaccharides were performed on a FACE system apparatus, as described in section 6.1.1. Urine creatinine was measured with a Beckman Creatinine Analyzer (Beckman Instruments, Fullerton, Calif.) using reagents supplied by Sigma Diagnostic Reagents (Sigma Chemical Co., St. Louis, Mo.).

6.2.2. Results

Figure 3:
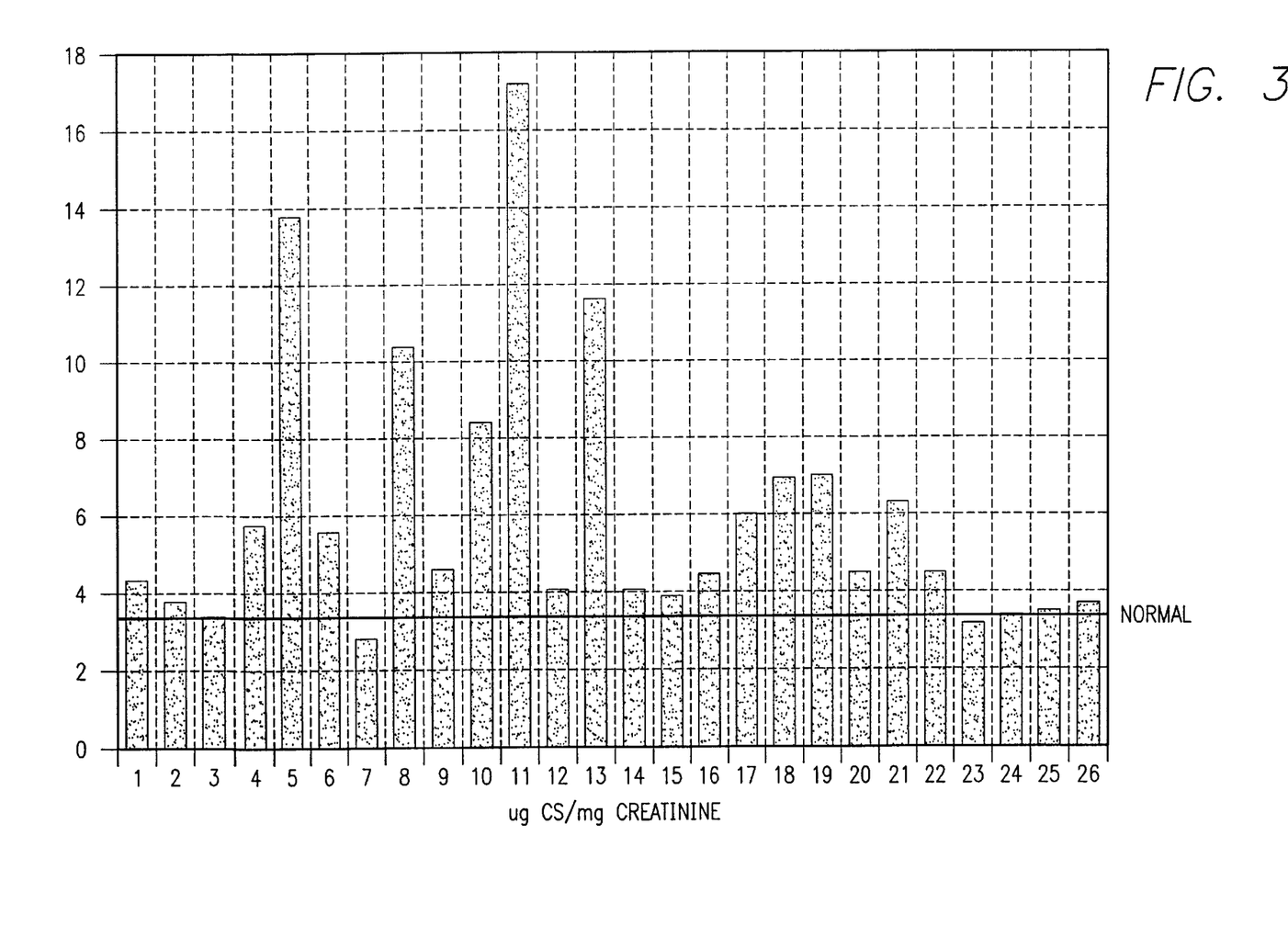
FIG. 3. Measurement of chondroitin sulfate in normal and osteoporotic women. Results are expressed as $\mu$g chondroitin sulfate (CS) per mg creatinine. Samples 23–26 are from normal, pre-menopausal women.

Results were expressed as micrograms of chondroitin sulfate disaccharide per mg of creatinine. The determinations from 26 samples are shown in FIG. 3. Patients 23–26 are normal, pre-menopausal females. As can be seen, the 4 normal samples cluster tightly around about 3.5 μg CS/mg creatinine. Elevated levels of chondroitin sulfate were detected in several patients, suggesting the occurrence of osteoporosis in these patients. The low variance in the controls suggests that a level above about 4 μg CS/mg creatinine, preferably above about 5 μg CS/mg creatinine, particularly preferably above about 6 μg CS/mg creatinine, more particularly preferably above about 8 μg CS/mg creatinine, even more particularly preferably above about 10 μg CS/mg creatinine, and still more particularly preferably above about 15 μg CS/mg creatinine in the samples indicates the occurrence of bone resorption in the subject.

6.3. Correlation of Urinary Chondroitin Sulfate and Collagen Telopeptide Levels in Normal and Osteoporotic Women The results from the chondroitin sulfate testing of patient urine samples were compared to the results from an FDA-approved test.

6.3.1. Materials and Methods

The Osteomark® (Ostex, Inc., Seattle, Wash.) test for n-telopeptides, an FDA-approved test for bone resorption, was performed on the identical samples described in section 6.2, following the manufacturer's instructions. Urine creatinine was measured with a Beckman Creatinine Analyzer (Beckman Instruments, Fullerton, Calif.) using reagents supplied by Sigma Diagnostic Reagents (Sigma Chemical Co., St. Louis, Mo.).

6.3.2. Results

Figure 4:
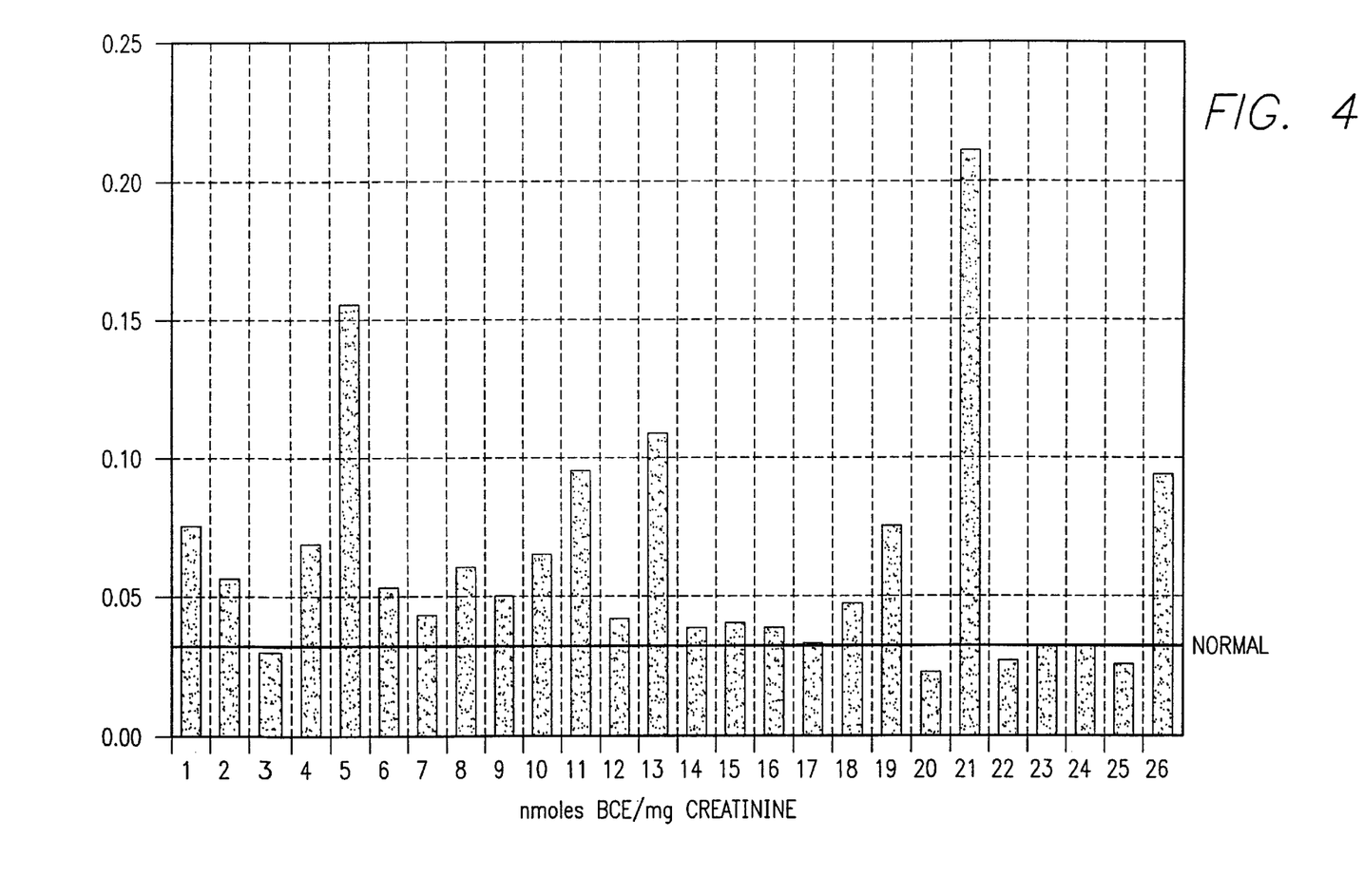
FIG. 4. Measurement of collagen telopeptides in normal and osteoporotic women. Results are expressed as nanomoles bovine collagen equivalents (BCE) per mg creatinine. Samples 23–26 are from normal, pre-menopausal women.

FIG. 4 shows the results of the Osteomark test. Patients 23–26 were normal, pre-menopausal females. As can be seen by comparing FIGS. 3 and 4, there was greater than 90% correlation between the presence or absence of an elevated level of chondroitin sulfate and the presence or absence of an elevated level of n-telopeptides in these 26 patients. This correlation suggested that the chondroitin sulfate assay was a viable test for osteoporosis. One normal subject (number 26) showed an elevated n-telopeptide level but a normal chondroitin sulfate level. Thus, the chondroitin sulfate method seemed to be more reproducible, and it may have had a lower false positive rate, than the FDA-approved Osteomark test.

6.4. Determination of Urinary Chondroitin Sulfate Levels From Normal Individuals and Patients with Osteoporosis Using Capillary Electrophoresis In this experiment, capillary electrophoresis was analyzed as an alternative to gel electrophoresis for determining chondroitin sulfate levels in human urine.

6.4.1. Materials and Methods

A urine sample from a patient with osteoporosis and a normal urine sample were obtained. GAGs were precipitated, digested, and labeled with ANTS as described in section 6.1.1. After labeling, the volume of the labeled oligosaccharides was brought to 200 μl by adding 190 μl of water.

Separation of the fluorescently tagged oligosaccharides was performed on a P/ACE system 5500 capillary electrophoresis apparatus (GLYKO, INC.) equipped with a diode array detector. Separations were performed by injecting a 4 nl aliquot into a 50 cm coated capillary electrophoresis column (Beckman Instruments, Fullerton, Calif.) running in 50 mM Acetate buffer, pH 10.4. Detection was performed by absorption at 214 nm.

6.4.2. Results

Figure 5A:
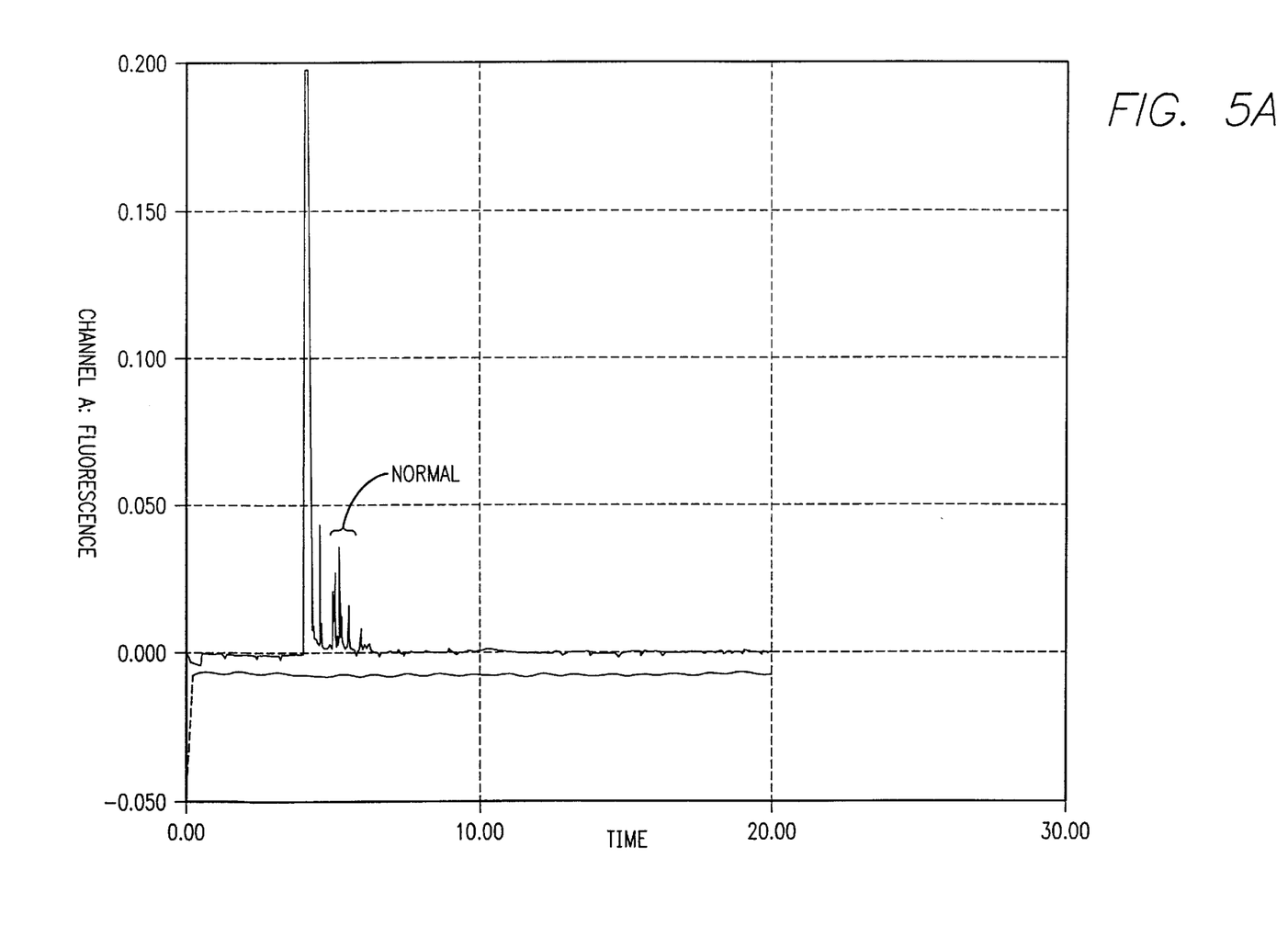
FIGS. 5A and 5B. Measurement of chondroitin sulfate levels in normal and osteoporotic women using capillary electrophoresis.
Figure 5B:
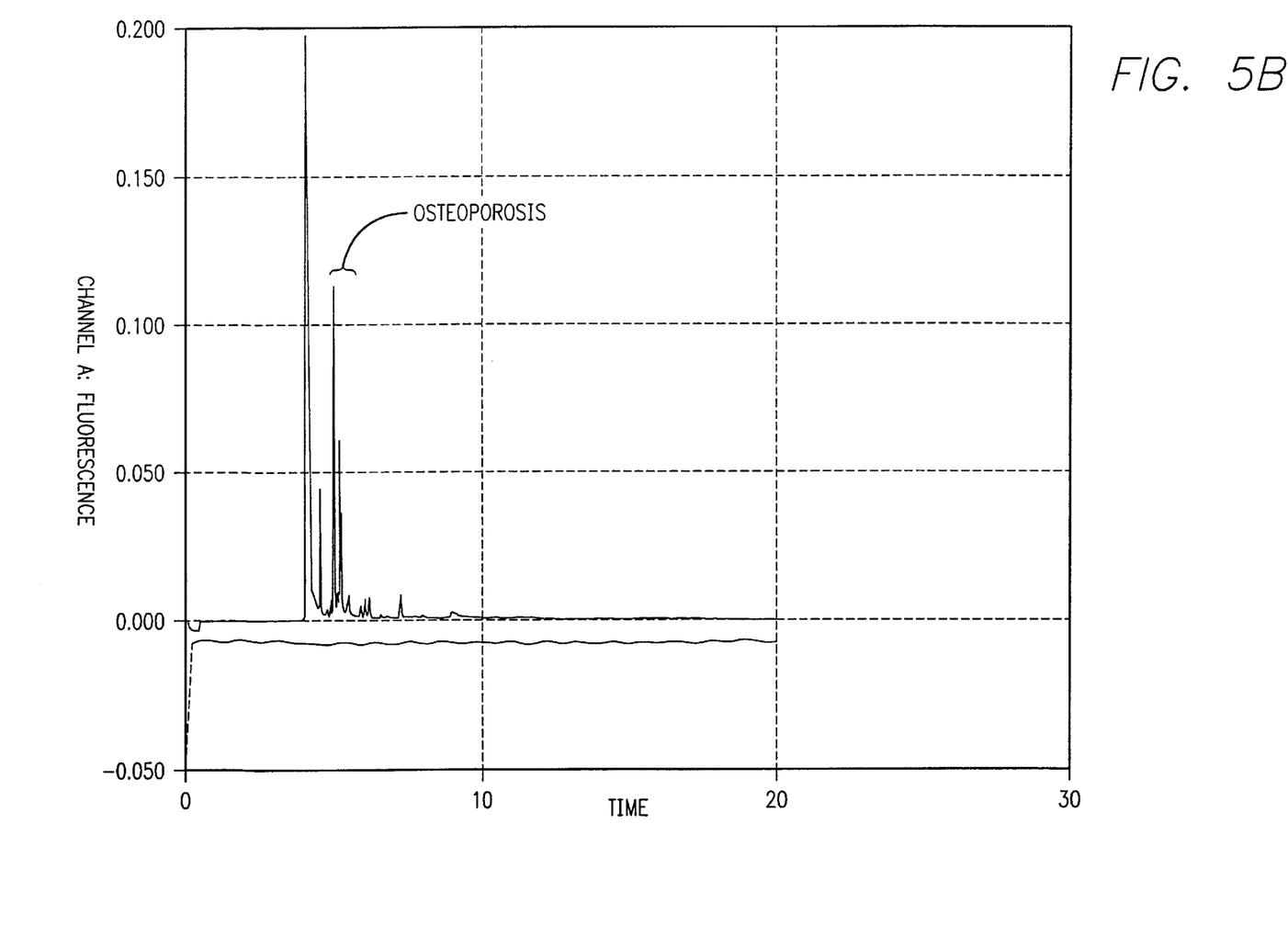

The electropherograms of the capillary electrophoresis detection of chondroitin sulfate disaccharides in the urine from normal and osteoporosis patients are shown in FIG. 5. As can be seen by comparing the peak heights in the figure, capillary electrophoresis distinguished quite clearly between a sample from a normal adult and a sample from an adult with osteoporosis. Thus, the chondroitin sulfate test is amenable to the use of capillary electrophoresis to distinguish between the levels of chondroitin sulfate in samples from a normal subject and from a patient with osteoporosis.

6.5. Measurement of Chondroitin Sulfate in Human Urine Using A Chromophore Label Labeling chondroitin sulfate with a chromophore tag is analyzed as an alternative to labeling with a fluorescent tag for determining chondroitin sulfate levels from human urine.

6.5.1. Materials and Methods

Urine sample from patients with osteoporosis and normal women are obtained. GAGs are precipitated and digested as described in section 6.1.1. The digested GAGs are then labeled with a chromophore. Chromophore-tagged oligosaccharides are separated from unbound label. Detection and quantitation of the chromophore-tagged oligosaccharides is performed on a UV-visible spectrophotometric device. Urine creatinine is measured with a Beckman Creatinine Analyzer (Beckman Instruments, Fullerton, Calif.) using reagents supplied by Sigma Diagnostic Reagents (Sigma Chemical Co., St. Louis, Mo.).

6.5.2. Results

Labeling of the chondroitin sulfate with a chromophore and quantitating the chromophore-labeled chondroitin sulfate is a viable method for detecting the occurrence of bone resorption in a subject.

The foregoing written specification is considered to be sufficient to enable one skilled in the art to practice the invention. Indeed, various modifications of the above-described modes for carrying out the invention which are obvious to those skilled in the field of clinical chemistry or related fields are intended to be within the scope of the following claims.

What is claimed is:

1. A composition comprising chondroitin sulfate disaccharide bound to a label by an antibody, wherein the chondroitin sulfate disaccharide is not part of a chondroitin sulfate chain.

* * * * *